United States Patent
Baxter et al.

(10) Patent No.: US 9,757,106 B2
(45) Date of Patent: Sep. 12, 2017

(54) DEGRADABLE EXPANDING CLOSURE PLUG

(71) Applicant: Cook Medical Technologies LLC, Bloomington, IN (US)

(72) Inventors: Charles Leland Baxter, West Lafayette, IN (US); Benjamin Marchi, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 585 days.

(21) Appl. No.: 14/064,691

(22) Filed: Oct. 28, 2013

(65) Prior Publication Data
US 2014/0155934 A1    Jun. 5, 2014

Related U.S. Application Data

(60) Provisional application No. 61/732,660, filed on Dec. 3, 2012.

(51) Int. Cl.
*A61B 17/08* (2006.01)
*A61B 17/00* (2006.01)

(52) U.S. Cl.
CPC ... *A61B 17/0057* (2013.01); *A61B 2017/00004* (2013.01); *A61B 2017/00592* (2013.01); *A61B 2017/00606* (2013.01); *A61B 2017/00623* (2013.01)

(58) Field of Classification Search
CPC ...... A61B 17/0057; A61B 2017/00575; A61B 2017/00592; A61B 2017/00606; A61B 2017/00623
See application file for complete search history.

(56) References Cited

U.S. PATENT DOCUMENTS

| | | |
|---|---|---|
| 4,031,569 A | 6/1977 | Jacob |
| 5,192,301 A | 3/1993 | Kamiya et al. |
| 5,342,393 A | 8/1994 | Stack |
| RE34,866 E | 2/1995 | Kensey et al. |
| 5,501,700 A | 3/1996 | Hirata |
| 5,578,045 A | 11/1996 | Das |
| 5,601,602 A | 2/1997 | Fowler |
| 5,620,461 A | 4/1997 | Muijs Van De Moer et al. |
| 5,916,236 A | 6/1999 | van de Moer |
| 5,968,075 A | 10/1999 | Wood |
| 5,976,174 A | 11/1999 | Ruiz |
| 6,077,281 A | 6/2000 | Das |

(Continued)

OTHER PUBLICATIONS

Dictionary.com definition for "adjacent" accessed Nov. 8, 2016; http://www.dictionary.com/browse/adjacent.*

(Continued)

*Primary Examiner* — Jonathan Miles
(74) *Attorney, Agent, or Firm* — Woodard, Emhardt, Moriarty, McNett & Henry, LLP (57) ABSTRACT

A device for closure of an opening in a medical patient's blood vessel wall is disclosed. It discloses a plug shaft which is: porous; blood absorbing; insertable in an opening in a blood vessel wall; and, at least partially comprises an ECM material. A first cap which is integral with the plug shaft at a proximal end thereof is disclosed. A second cap is integral with the plug shaft. An insertion tube, a pusher, surgical methods of use, and kits, are also disclosed.

20 Claims, 6 Drawing Sheets (56) References Cited

U.S. PATENT DOCUMENTS

| | | | |
|---|---|---|---|
| 6,126,675 | A | 10/2000 | Shchervinsky et al. |
| 6,786,915 | B2 | 9/2004 | Akerfeldt et al. |
| 7,931,671 | B2 | 4/2011 | Tenerz |
| 8,105,352 | B2 | 1/2012 | Egnelov |
| 8,192,457 | B2 | 6/2012 | Coleman et al. |
| 8,992,567 | B1 * | 3/2015 | Houser ................ A61B 17/08 606/213 |
| 2003/0014126 | A1 | 1/2003 | Patel et al. |
| 2004/0049207 | A1 * | 3/2004 | Goldfarb ............ A61B 17/0401 606/139 |
| 2004/0133236 | A1 | 7/2004 | Chanduszko |
| 2004/0215231 | A1 | 10/2004 | Fortune et al. |
| 2005/0288706 | A1 * | 12/2005 | Widomski ......... A61B 17/0057 606/213 |
| 2006/0210597 | A1 | 9/2006 | Hiles |
| 2007/0083231 | A1 | 4/2007 | Lee |
| 2008/0097509 | A1 | 4/2008 | Beyar et al. |
| 2009/0148492 | A1 | 6/2009 | Dave et al. |
| 2009/0171387 | A1 | 7/2009 | Pipenhagen et al. |
| 2009/0216267 | A1 | 8/2009 | Willard et al. |
| 2009/0318955 | A1 | 12/2009 | Dave et al. |
| 2010/0030246 | A1 * | 2/2010 | Pavcnik ............ A61B 17/0057 606/157 |
| 2010/0179589 | A1 | 7/2010 | Roorda et al. |
| 2011/0066181 | A1 | 3/2011 | Jenson et al. |
| 2011/0213415 | A1 | 9/2011 | McGuckin, Jr. et al. |
| 2012/0022585 | A1 | 1/2012 | Atanasoska et al. |
| 2012/0143243 | A1 | 6/2012 | Hill et al. |

OTHER PUBLICATIONS

TheFreeDictionary.com definition for "domed" accessed Nov. 8, 2016; http://www.thefreedictionary.com/domed.*

* cited by examiner

DEGRADABLE EXPANDING CLOSURE PLUG

CROSS-REFERENCE TO RELATED APPLICATIONS

This application claims the benefit of U.S. Provisional Application No. 61/732,660, filed Dec. 3, 2012, which is hereby incorporated by reference in its entirety.

BACKGROUND

The present invention relates to closing openings in a blood vessel wall.

The device may be used as a replacement to the traditional practice of using pressure to establish acute hemostasis following a vascular procedure making use of percutaneous access with a large delivery device.

Various devices are known for closing openings in blood vessels. For example, Abbotts Perclose suture delivery devices have been used. Other devices are disclosed in U.S. Patent Publication Nos. US 2009/0318955 A1, US 2009/0171387 A1, US 2009/0148492 A1, US 2008/0097509 A1, US 2004/0215231 A1, U.S. Pat. No. 5,601,602 and others. The devices take a variety of different approaches to closing tissue walls.

There is a need for improvement in this field including providing acute hemostasis, and an environment for a rapid healing process.

SUMMARY

The invention is defined in the claims, and only the claims. This summary is not limiting. The invention may include one or more of a device for closure of an opening in a medical patient's blood vessel wall. It may include some or all of a plug shaft which preferable is one or more of: porous; blood absorbing; insertable in an opening in a blood vessel wall; at least partially comprises an ECM material; and, expands in the opening. It may include a first cap which is integral with the plug shaft at a proximal end thereof and which: is larger in average radius than the plug shaft; and; is compressible from the larger diameter, and a second cap which is integral with the plug shaft at a distal end thereof and which: is larger in average radius than the plug shaft; and; is compressible from the larger diameter.

The invention may include a tube, a pusher, methods of use, and kits, as claimed.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. While aspects of embodiment(s) may be shown in detail, it will be apparent to those skilled in the relevant art that some features that are not required for the present invention.

Examples are shown in FIGS. 1-8, described below. As used herein, the following terms are defined, for purposes of the claims and of the written description:

The term "bio-degradable" means able to be broken down and absorbed in, reabsorbed and/or passed from the human body.

The term "blood vessel" means artery or vein.

The terms "depth" or "length" means the average distance of an element taken in a direction proximal to distal.

The term "diameter" means twice the "radius" as defined herein.

The term "distal" means, relative to a reference, toward the doctor or other operator of the device; normally the opposite of "proximal".

The term "ECM material" means material (sheet, solid shape, powder, liquid or otherwise) harvested from a (previously) living animal which is an extracellular matrix, including collagen. This includes without limitation material harvested from the walls of animal intestine, bladder, liver, and stomach.

The term "load" or "loaded" means placed into position prior to insertion into a patient.

The term "proximal" means, relative to a reference, away from the doctor or other operator of the device; normally the opposite of "distal".

The term "radius" means the average distance of an element taken in a direction from the center to the perimeter.

The term "small intestine submucosa" means material (sheet, solid shape, powder, liquid or otherwise) which is entirely or partially made up of portions of the submucosal layer of an animal's small intestines.

Otherwise, words herein have their ordinary meaning as defined in *Merriam-Webster's Collegiate Dictionary*, Tenth Edition.

Figure 1:
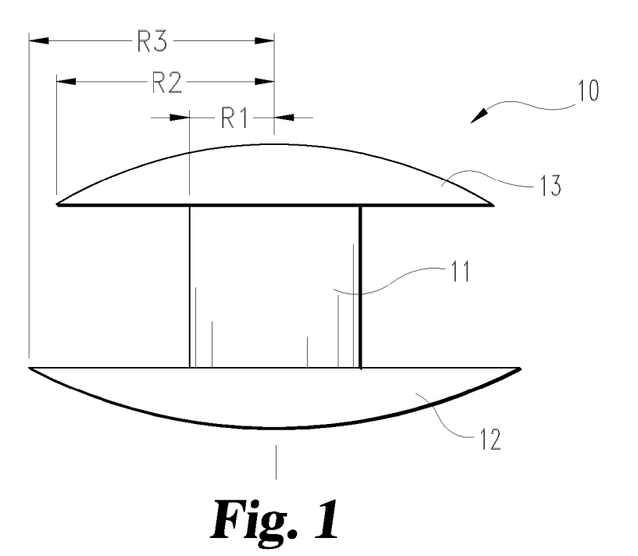
FIG. 1 is side view of one example of a plug usable in the invention.
Figure 2:
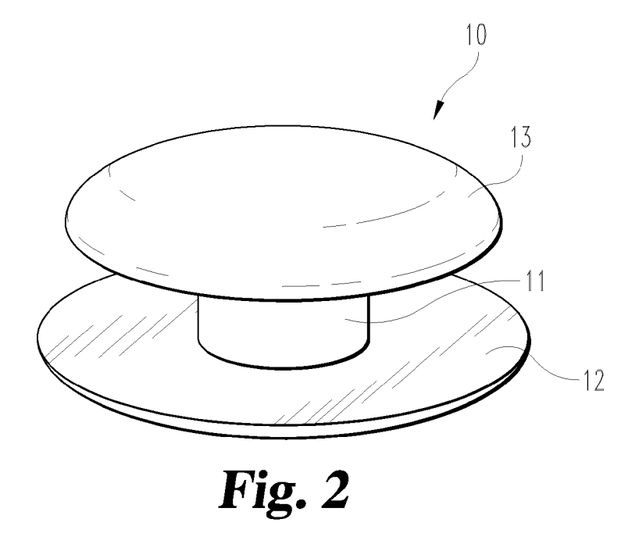
FIG. 2 is a perspective view of the plug of FIG. 1.
Figure 3:
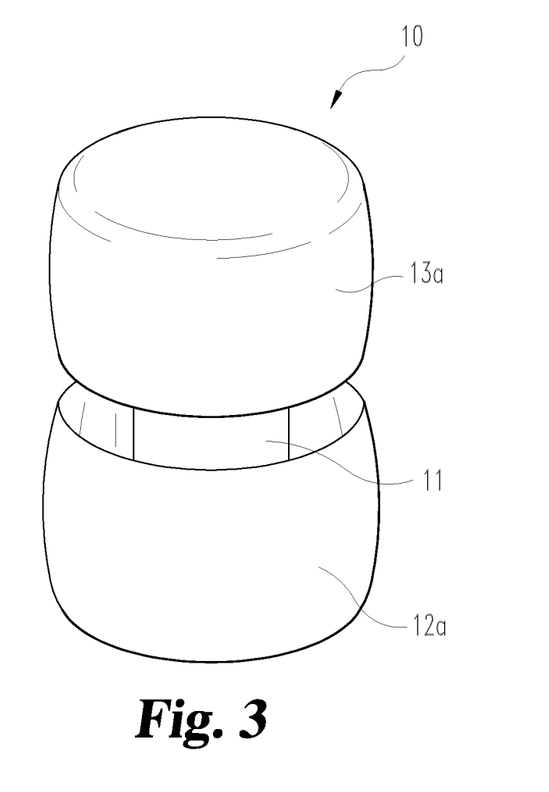
FIG. 3 is a perspective view of the plug of FIG. 2 with the caps compressed radially inward.
Figure 4A:
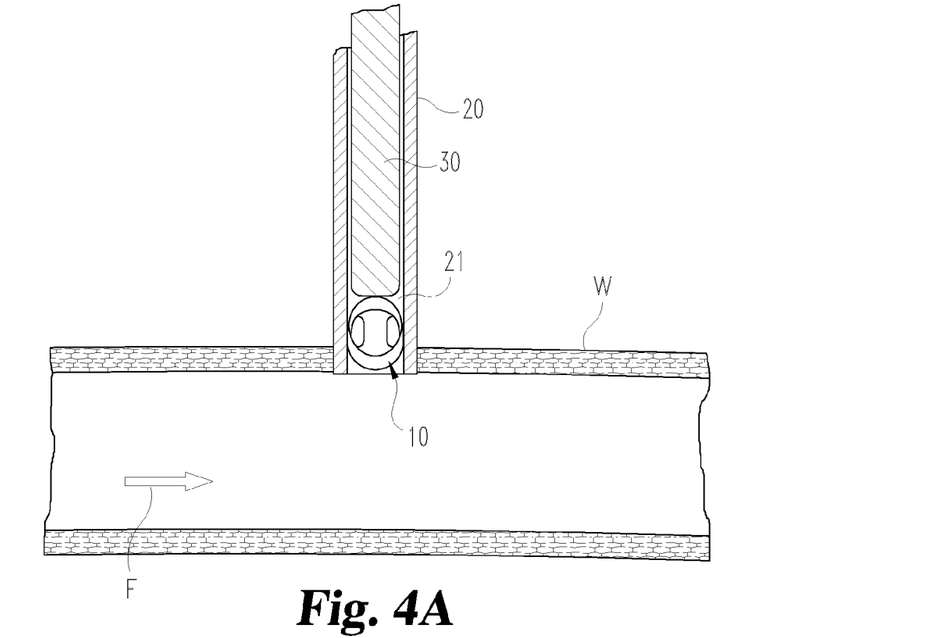
FIGS. 4A-4C are, in sequence, side cross sectional views of a device and plug, and acts of use thereof, for plugging a blood vessel.
Figure 4B:
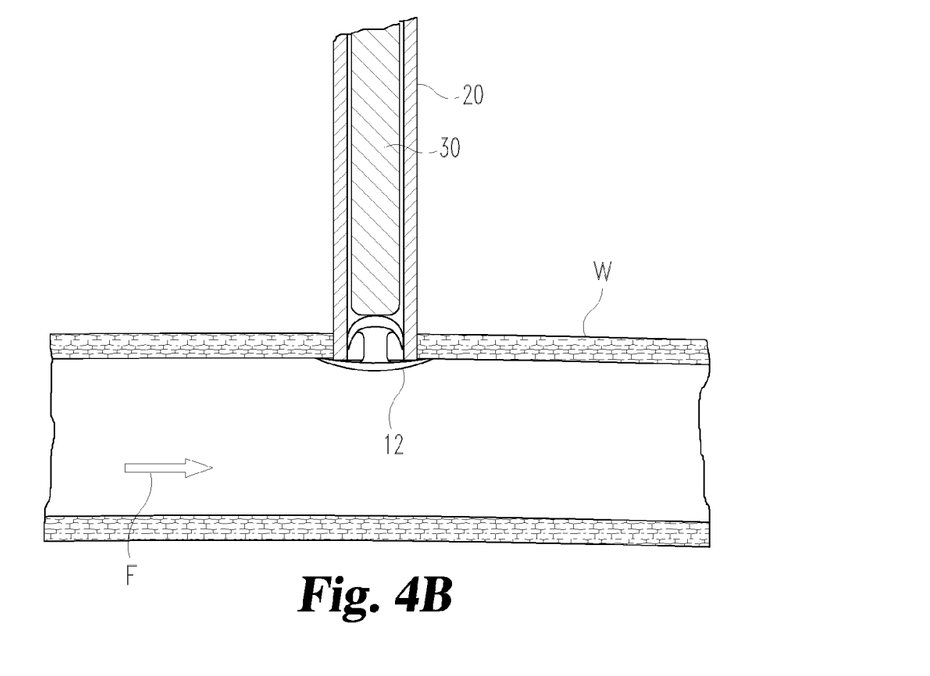
Figure 4C:
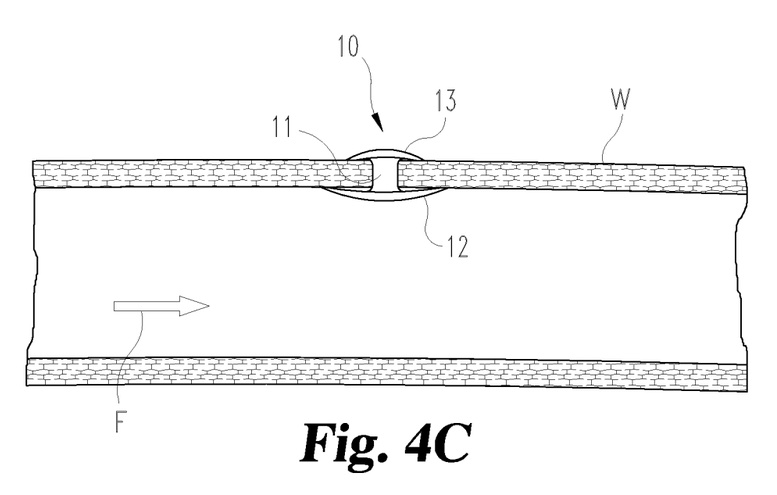
Figure 5:
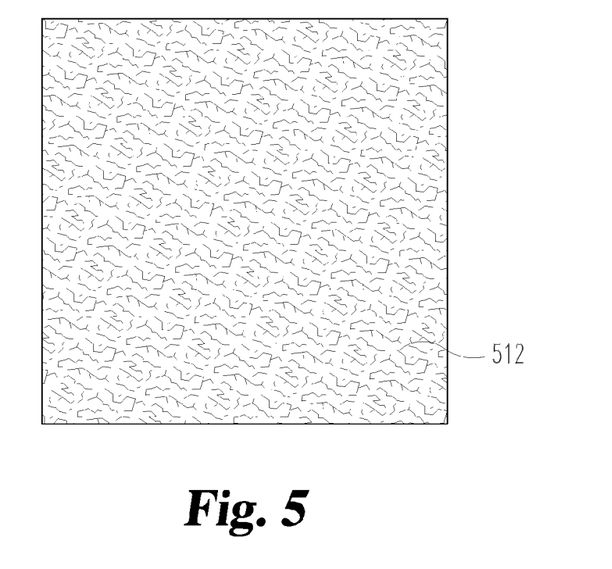
FIGS. 5-8 are plan views of alternative cap shapes.
Figure 6:
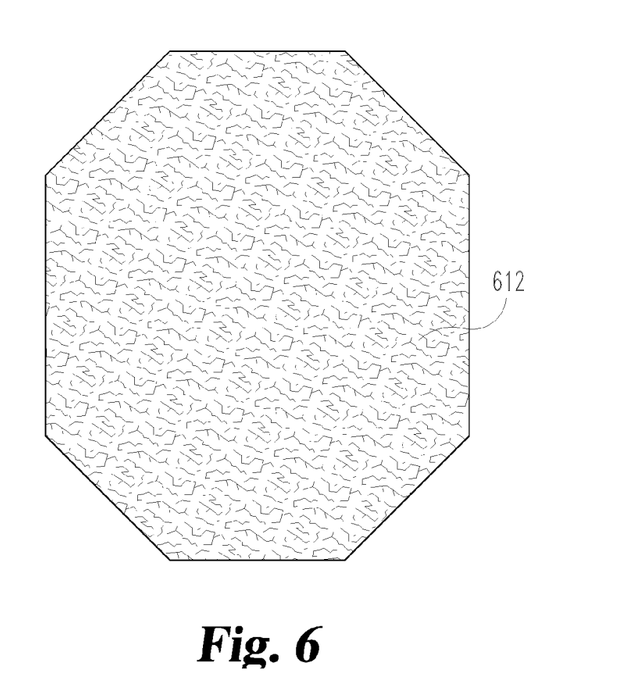
Figure 7:
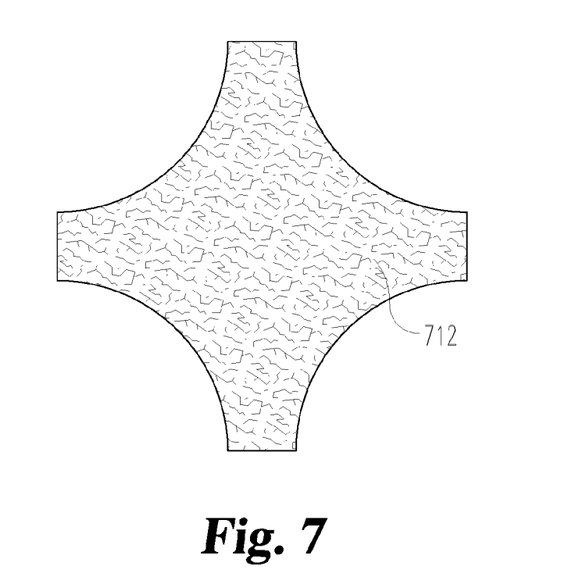
Figure 8:
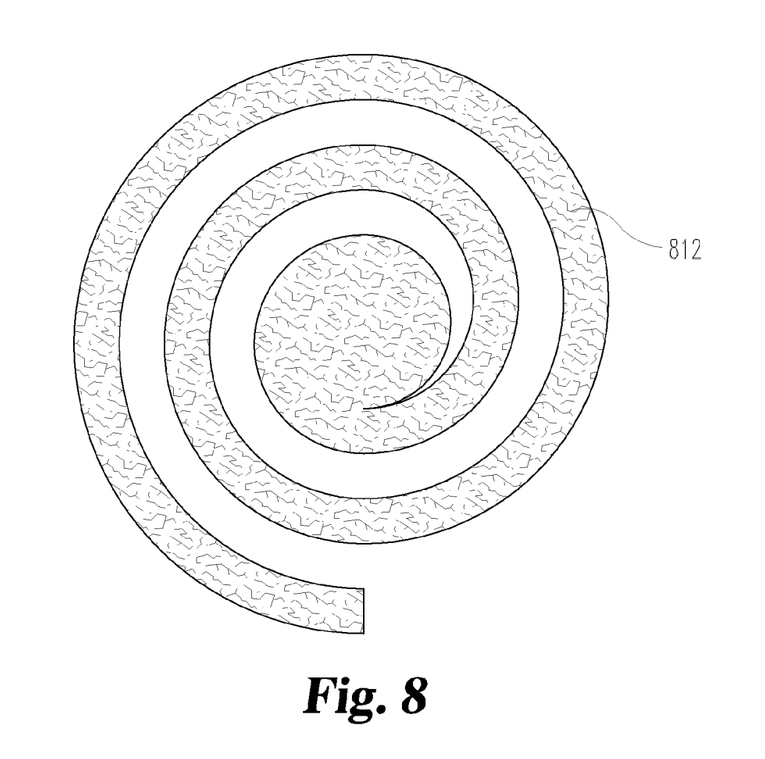

An example plug device 10 (see FIGS. 1-3) for closure of an opening in a medical patient's blood vessel wall W is shown. Note that blood flow F is shown in FIGS. 4A-4C. The plug may include some or all of a plug shaft 11 which preferable is one or more of: (i) porous; (ii) blood absorbing; (iii) insertable in an opening in a blood vessel wall; and, (iv) at least partially comprises an ECM material. Plug 10 also includes a first cap 12 which is integral with said plug shaft at a proximal end thereof and which: (i) is larger in average radius R2 than said plug shaft R1; and; (ii) is compressible from said larger diameter. The plug also includes a second cap 13 which is integral with said plug shaft 11 at a distal end thereof and which: (i) is larger in average radius R3 than said plug shaft R1; and; (ii) is compressible from said larger diameter. Optionally, one or both caps 12, 13 may have a slightly domed outer shape as illustrated in FIGS. 1 and 2, although other shapes (e.g. flat discs or otherwise) are also available.

The device of may further include a tube 20 having a lumen 21, with said plug shaft 11, first cap 12 and said second cap 13 are loadable in lumen 21 (see FIG. 4A) with at least the first and second caps compressed within said lumen. Note that plug 10 is shown in isolation with its caps compressed, such as by folding back, in FIG. 3 showing cap 12 as folded cap 12a and cap 13 as folded cap 13a. Other forms of compression, such as axial squeezing, coiling (see e.g. cap of FIG. 8) and otherwise are likewise optional. A separate pusher 30 movable through lumen 21 to push said plug shaft, first cap and said second cap out of a distal end of said lumen (FIGS. 4A-4C).

In one optional version, the device the distal second cap 12 is: (i) porous; (ii) blood absorbing; (iii) insertable in a blood vessel; and, (iv) at least partially comprises an ECM material. This may or may not be combined with the further optional features of proximal first cap 13 is: (i) porous; (ii) blood absorbing; and, (iii) at least partially comprises an ECM material.

An optional material choice is with the ECM material including at least some porcine small intestine submucosa. Optionally, the plug shaft, proximal first cap, and/or distal second cap may be made substantially of a unitary piece of bio-degradable solid foam. However, for example, they may be formed entirely of ECM material molded and/or shaped into a plug. Moreover, regardless of solid foam or other material, the plug shaft, proximal first cap, and/or the distal second cap may be impregnated, and/or coated with powdered ECM material (even if the powdered material is or is not liquid born during application).

Preferably, the plug 10 (including some or all of its shaft and/or caps) will expand when exposed to liquid, such as blood or water. This provides for expansion in situ in the wall W opening, providing for snug sealing against outflow of most blood while clotting and healing occur. Preferably, the shaft 11 is solid. However, optionally it may have a longitudinal lumen (not shown) through it large enough to accommodate a guide wire. In such case, upon withdrawal of the guide wire the expansion of the shaft also expands inwardly to close such lumen again outward blood flow.

Dimensions may vary, but preferably the plug shaft 11 has an average diameter of about 3 to 4 millimeters and a length of about 1 to 2 millimeters; the proximal first cap 13 has an average diameter of about 5 to 8 millimeters and a depth of about 1 to 2 millimeters; and, the distal second cap 12 has an average diameter of about 5 to 8 millimeters and a depth of about 1 to 2 millimeters. Even more preferably the proximal first cap 13 has an average diameter of about 6 to 8 millimeters and a depth of about 1 to 1.5 millimeters; and, the distal second cap 12 has an average diameter of about 5 to 6 millimeters and a depth of about 1 millimeters.

While one or both caps may be round as shown in FIG. 2, they may be any other shape so long as their radius (i.e. average radius) is larger than that of the shaft. In addition to circular, elliptical, oblong, the shapes of caps may include, as illustrated in FIGS. 5-8, rectangular cap 512, octagonal cap 612, cross shaped cap 712, coiled cap 812, or otherwise. The caps may be the same shape or different shape from each others. They may be the same size or different, such as the first cap larger or smaller in radius than the second cap. Also, the shaft 11 may be any shape, such as cylindrical, octagonal, rectangular, cross shaped or otherwise. As defined, the radii of such shapes is the average radius thereof. Optionally, a lanyard (such as made of suture, ECM material or other material) may be attached as part of the plug and the lanyard secured to tissue outside of the vessel to act a redundant securing against the plug migrating through the vessel were it to be knocked loose.

One or more of the forgoing may be provided in a kit. The kit is for closure of an opening in a medical patient's vessel wall comprising the devices of any preceding description and/or figures, and surgically sterilized and contained within a sterile package. For example, a kit may include a tube 20, a pusher and a plug 10. The plug may be already loaded within the tube within the kit packaging. A selection of two or more plugs of various size may be included in the kit, either separate from the tube(s) or loaded into their own dedicated tube within the sterile kit.

The use of the device may include a surgical method for closure of an opening in a medical patient's blood vessel wall, including the acts of inserting a tube 20 into the opening in the blood vessel wall W, the tube having been loaded with a plug of the types previously described. Then, this is followed by the act of pushing the plug out of a distal end of said tube with a separate pusher, wherein said second cap expands within the blood vessel and said first cap expands outside of the blood vessel.

This may be done after procedures using percutaneous access for vascular procedures the access site must be closed. This method not only may provide acute hemostasis, but also an environment for a rapid healing process. This device provides both effective acute hemostasis and a matrix for effective long term healing of the arterial wall. The device is inserted in a compressed state and the "cap" expands inside the vessel as it encounters fluid (in this case blood). The sheath over the device is pulled back over the device exposing the "shaft" which fills the opening in the wall of the vessel. The shaft, being made of the same material, expands as it encounters moisture providing a tight seal and consistent contact with the wall of the vessel. As the sheath is pulled back yet further a smaller "retention cap' is exposed and also expands. The retention cap may require a small amount of liquid be introduced via the sheath to expand correctly. Once full expanded the device effectively fills the opening in the wall of the vessel. Additionally the two caps on the device anchor it securely in the wall of the vessel. As blood is absorbed into the pores of the device coagulation begins quickly helping to eliminate any seepage through the porous material. The material the device consists of compressible, degradable solid foam with SIS of other ECM material incorporated in the casting of the solid foam. The SIS provides a matrix for cell in-growth and effectively anchors the device into the wall of the vessel.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A device for use to provide closure of an opening in a medical patient's blood vessel wall, including:
   (a) an implantable plug device which includes a unitary body of biodegradable solid foam cast from a casting material including an extracellular matrix (ECM) material, said unitary body of biodegradable solid foam including a plug shaft, a first cap and a second cap, wherein said first cap defines a proximal-most surface of said implantable plug device, and wherein said second cap defines a distal-most surface of said implantable plug device;

wherein said plug shaft is: (i) porous; (ii) blood absorbing; (iii) insertable in an opening in a blood vessel wall; and (iv) expands in the opening;

wherein said first cap is integral with said plug shaft at a proximal end thereof and: (i) is larger in average radius than said plug shaft; and; (ii) is compressible from a larger diameter to a smaller diameter;

wherein said second cap is integral with said plug shaft at a distal end thereof and: (i) is larger in average radius than said plug shaft; and; (ii) is compressible from a larger diameter to a smaller diameter;

(b) a tube having a lumen, wherein said plug shaft, said first cap and said second cap are loaded in said lumen with at least said first and said second caps compressed within said lumen with said first cap having a periphery folded in a distal direction to extend distally alongside said plug shaft and said second cap having a periphery folded in a proximal direction to extend proximally alongside said plug shaft; and (c) a pusher received in said lumen, wherein said pusher has a distal end surface positioned against said proximal-most surface of said implantable plug device defined by said first cap, and wherein said pusher is movable in said lumen to push said implantable plug device out of a distal end of said lumen.

2. The device of claim 1 wherein said first cap has a domed outer shape defining said proximal-most surface of said implantable plug device.

3. The device of claim 2 wherein said first cap is smaller in radius than said second cap.

4. The device of claim 1, wherein said second cap is: (i) porous; (ii) blood absorbing; and, (iii) insertable in a blood vessel.

5. The device of claim 4, wherein said first cap and said second cap each have a domed outer surface.

6. The device of claim 1, wherein said ECM material includes at least some porcine small intestine submucosa.

7. A device of claim 1, wherein:
said plug shaft has an average diameter of about 3 to 4 millimeters and a length of about 1 to 2 millimeters;
said first cap has an average diameter of about 5 to 8 millimeters and a depth of about 1 to 2 millimeters; and,
said second cap has an average diameter of about 5 to 8 millimeters and a depth of about 1 to 2 millimeters.

8. A device of claim 1, wherein said plug shaft, said first cap, and said second cap are made entirely of the ECM material.

9. A device of claim 1, wherein said plug shaft, said first cap, and said second cap are impregnated with powdered ECM material.

10. The device of claim 1, wherein said each of said plug shaft said first cap and said second cap does not have a lumen extending longitudinally therein.

11. A kit for closure of an opening in a medical patient's blood vessel wall comprising the device of claim 1 surgically sterilized and contained within a sterile package.

12. A method of closure of an opening in a medical patient's blood vessel wall comprising the acts of providing a device of claim 1 and inserting in a medical patient said plug shaft, said first cap and said second cap, said inserting including pushing said plug shaft, said first cap and said second cap from said distal end of said lumen to position said second cap on a first side of the vessel wall, said plug shaft within the opening, and said first cap on a second side of the vessel wall opposite the first side of the vessel wall.

13. A device for use to provide closure of an opening in a medical patient's blood vessel wall, including:
a tube having a lumen;
an implantable plug device loaded within said lumen, said implantable plug device including a unitary body of biodegradable solid foam cast from a casting material including an extracellular matrix (ECM) material, said unitary body of biodegradable solid foam having a plug shaft, a first cap and a second cap, wherein said first cap and said second cap are compressed within said lumen, wherein said first cap has a domed outer shape defining a proximal-most surface of said implantable plug device and said second cap has a domed shape defining a distal-most surface of said implantable plug device;
a pusher received in said lumen, wherein said pusher has a distal surface received against said proximal-most surface of said implantable plug device defined by said domed outer shape of said first cap, wherein said pusher is movable through said lumen to push said implantable plug device out of a distal end of said lumen;
wherein said plug shaft is: (i) porous; (ii) blood absorbing; (iii) insertable in an opening in a blood vessel wall; and (iv) expands in the opening;
wherein said first cap is integral with said plug shaft at a proximal end thereof and said first cap: (i) is larger in average radius than said plug shaft; and; (ii) is compressed from a larger diameter to a smaller diameter within said lumen to assume a condition wherein an outer periphery of said first cap is folded in a distal direction to extend distally alongside said plug shaft;
wherein said second cap is integral with said plug shaft at a distal end thereof and said second cap: (i) is larger in average radius than said plug shaft; and; (ii) is compressed from a larger diameter to a smaller diameter within said lumen.

14. The device of claim 13, wherein said second cap is: is compressed from a larger diameter to a smaller diameter within said lumen to assume a condition wherein an outer periphery of said second cap is folded in a proximal direction to extend proximally alongside said plug shaft.

15. The device of claim 14, wherein said first cap is smaller in radius than said second cap.

16. The device of claim 15, wherein said ECM material includes at least some porcine small intestine submucosa.

17. A device of claim 15, wherein:
said plug shaft has an average diameter of about 3 to 4 millimeters and a length of about 1 to 2 millimeters;
said first cap has an average diameter of about 5 to 8 millimeters and a depth of about 1 to 2 millimeters; and,
said second cap has an average diameter of about 5 to 8 millimeters and a depth of about 1 to 2 millimeters.

18. The closure device of claim 13, wherein each of said plug shaft, said first cap and said second cap does not have a lumen extending longitudinally therein.

19. A kit for closure of an opening in a medical patient's blood vessel wall comprising the device of claim 17 surgically sterilized and contained within a sterile package.

20. A method of closure of an opening in a medical patient's blood vessel wall comprising the acts of providing a device of claim 13 and pushing said plug device out of said distal end of said lumen to position said plug device with said second cap on a first side of the vessel wall, said plug shaft within the opening, and said first cap on a second side of the vessel wall opposite the first side of the vessel wall.

* * * * *